US006969351B2

(12) United States Patent
Knoll

(10) Patent No.: US 6,969,351 B2
(45) Date of Patent: Nov. 29, 2005

(54) DEVICE AND METHOD FOR REMOVING LIQUID FROM ENDOGENIC TISSUE AND DETERMINING THE CONCENTRATIONS OF SUBSTANCE IN SAID LIQUID

(75) Inventor: Meinhard Knoll, Geschwister-Scholl-Strasse-9, Steinfurt (DE) 48565

(73) Assignee: Meinhard Knoll, Steinfurt (DE)

( * ) Notice: Subject to any disclaimer, the term of this patent is extended or adjusted under 35 U.S.C. 154(b) by 48 days.

(21) Appl. No.: 10/182,123

(22) PCT Filed: Jan. 10, 2001

(86) PCT No.: PCT/DE01/00106

§ 371 (c)(1),
(2), (4) Date: Dec. 10, 2002

(87) PCT Pub. No.: WO01/54570

PCT Pub. Date: Aug. 2, 2001

(65) Prior Publication Data

US 2003/0109807 A1   Jun. 12, 2003

(30) Foreign Application Priority Data

Jan. 27, 2000   (DE) ................................ 100 03 507

(51) Int. Cl.[7] ............................. A61B 5/00; A61B 5/02
(52) U.S. Cl. ....................... 600/309; 600/583; 600/365
(58) Field of Search ................... 600/316, 365, 600/573, 578, 583, 584, 309

(56) References Cited

U.S. PATENT DOCUMENTS

| 4,151,832 | A | | 5/1979 | Hamer |
| 5,322,063 | A | * | 6/1994 | Allen et al. .................. 600/316 |
| 5,582,184 | A | | 12/1996 | Erickson et al. |
| 5,782,871 | A | | 7/1998 | Fujiwara et al. |
| 5,804,048 | A | * | 9/1998 | Wong et al. ........... 204/403.09 |
| 5,820,570 | A | | 10/1998 | Erickson et al. |
| 5,846,392 | A | | 12/1998 | Knoll |
| 5,902,253 | A | * | 5/1999 | Pfeiffer et al. .............. 600/584 |
| 6,027,459 | A | * | 2/2000 | Shain et al. ................. 600/573 |
| 6,045,541 | A | * | 4/2000 | Matsumoto et al. ........ 600/573 |
| 6,058,321 | A | * | 5/2000 | Swayze et al. ............. 600/310 |
| 6,334,856 | B1 | * | 1/2002 | Allen et al. .................. 604/191 |

FOREIGN PATENT DOCUMENTS

| DE | 26 11 721 B2 | 10/1978 |
| DE | 44 08 352 | 9/1995 |
| DE | 197 08 256 A1 | 9/1997 |
| DE | 195 49 316 C2 | 3/1998 |

(Continued)

OTHER PUBLICATIONS

Webster's II New Riverside University Dictionary, Riverside Publishing Co., 1994, p. 450 and 636.*

Primary Examiner—Eric F. Winakur
Assistant Examiner—Matthew J Kremer
(74) Attorney, Agent, or Firm—Leydig, Voit & Mayer, Ltd.

(57) ABSTRACT

The present invention relates to a device for removing liquid from endogenic tissue and determining concentrations of substances in this liquid, in which a hollow chamber (3), which is placeable in direct contact on the skin (1) covering the tissue with at least one contact opening (3.1) disposed on a contact surface (3.2) and the hollow chamber (3) is connected to a low pressure-producing element (P) via a channel (4.1).

28 Claims, 11 Drawing Sheets

FOREIGN PATENT DOCUMENTS

Figure 1:
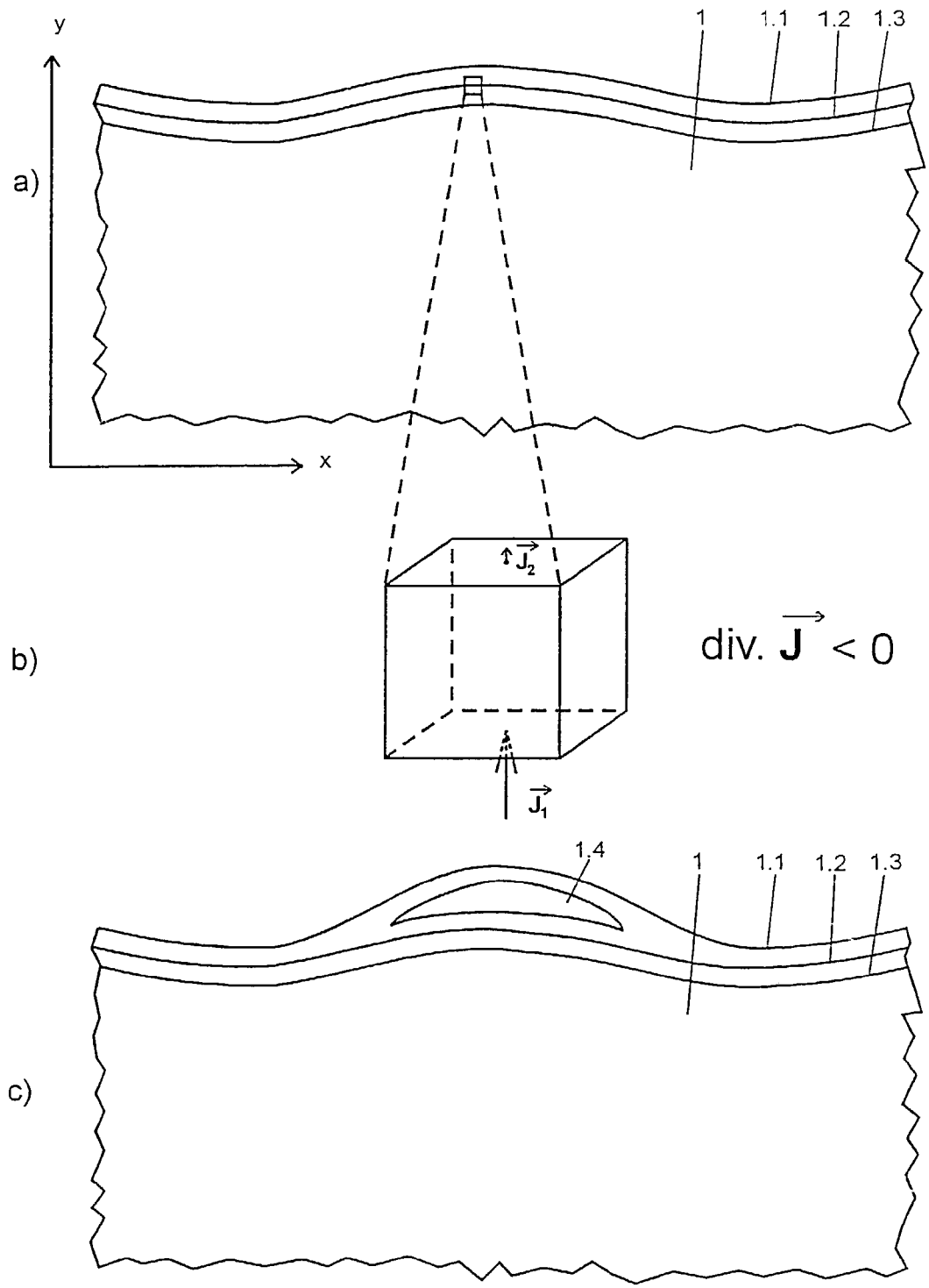

| | | |
|---|---|---|
| DE | 44 26 694 C2 | 7/1998 |
| DE | 198 48 112 | 6/2000 |
| EP | 330 472 | 8/1989 |
| EP | 513 789 | 11/1992 |
| EP | 555 554 | 8/1993 |
| EP | 595 237 | 5/1994 |
| WO | WO 96/00614 | 1/1996 |
| WO | WO 98/24366 | 6/1998 |
| WO | WO 99/27852 | 6/1999 |
| WO | WO99/52433 | * 10/1999 ............ A61B 5/14 |

* cited by examiner

DEVICE AND METHOD FOR REMOVING LIQUID FROM ENDOGENIC TISSUE AND DETERMINING THE CONCENTRATIONS OF SUBSTANCE IN SAID LIQUID

The invention relates to a device and a method for removing liquid from endogenic tissue and determining the concentrations of substances in this liquid, the removal being able to be effected directly on a human body. Subsequent to the removal of such a liquid, which is in particular lymph, the concentration of substances contained in this lymph, such as for example the determination of glucose concentration by means of suitable sensors or sensor systems, can then be implemented.

In order to determine the glucose concentration in subcutaneous tissue, it is known from DE 44 26 694 C2 to implant a microdialysis needle underneath the skin surface. By means of this microdialysis needle, glucose from the lymph is brought through a dialysis membrane into a perfusate flow and with the latter transports the glucose to a sensor with which its concentration can be measured.

Furthermore, the use of ultrafiltration probes, in which the glucose recovery is intended to be effected by means of an ultrafiltration membrane, was proposed by D. Moskone i.a. in "Ultrafiltrate sampling device for continuous monitoring"; in Medical and Biological Engineering and Computing; (1996); volume 34; pages 290 to 294. With such a solution, volume flows in the range of approximately 100 nl/min can be achieved.

In the unpublished German Patent Application DE 198 48 112.8, a minimally invasive sensor system is described in which merely perforated hollow probes without dialysis or ultrafiltration membranes are intended to be used for removing lymph from the subcutaneous tissue.

In U.S. Pat. Nos. 5,582,184 and 5,820,570 solutions are mentioned in which lymph can be removed by means of a very thin hollow needle. This hollow needle is pierced through the uppermost layer of skin and, by applying a low pressure, the lymph can be removed by means of the very thin hollow needle.

With the known solutions, it is however required in every case either to implant a probe underneath the skin or to pierce the skin in order to remove liquid from the tissue or from the body of a human. The conventional microdialysis and ultrafiltration probes are however not sufficiently stable. Therefore so-called introduction aids must be inserted into the tissue for the implantation or the introduction. These probes or systems are correspondingly costly.

It can be maintained in general that the conventional solutions are only accepted with difficulty by corresponding patients since in every case the uppermost skin layer or skin layers must be correspondingly perforated, which is painful and the insertion or implanting depth only being able to be checked with difficulty. Furthermore, the operation hereby often produces blood.

It is therefore the object of the invention to propose possibilities for removing liquids from the endogenic tissue in a non-bloody and controlled manner, the concentrations of substances thereof being able to be determined without the implantation of a probe being required and making available with simply constructed and cost-effective means a solution which is also appropriate for continuous measurements.

According to the invention, this object is achieved by the features of claim 1 for a device and with the features of claim 25 for a corresponding method. Advantageous embodiments and developments of the invention are produced by application of the features mentioned in the subordinate claims.

With the solution according to the invention, the removal of a liquid, this liquid subsequently being called however lymph in general for this purpose, is removed from endogenic tissue without a probe or another needle-shaped element, through the interior of which the removed lymph is guided to a sensor, being used. This leads to a substantially smaller inconvenience for the respective patient since the removal is effected in a non-invasive or minimally invasive manner and if the skin must be penetrated at all this occurs to an extremely small degree virtually without pain.

A device is used for this purpose which has a contact surface which can be placed directly on the skin covering the respective tissue. At least one hollow chamber is configured in the device and has at least one contact opening which is disposed on the contact surface. By means of an element producing low pressure, the pressure can be lowered in the hollow chamber so that a pressure difference occurs between the tissue and the skin covering the tissue and the hollow chamber. The drop in pressure can be implemented once or else repeatedly.

This pressure difference leads to the fact that a pressure gradient acts vertically in the skin layers situated thereunder which produces flows of lymph in the skin. By means of liquid divergence within the skin, which is formed from a plurality of layers, a liquid reservoir with lymph is formed underneath the uppermost skin layer in the region of one contact opening or also of a plurality of contact openings. At the same time, the uppermost layer of skin is arched in the direction of the device according to the invention.

When there is sufficient pressure difference, lymph passes into the hollow chamber and is conveyed via a channel in the direction of the element producing low pressure. It can be required if necessary to slightly penetrate at least the uppermost layer of skin in order to enable, to facilitate or to increase the liquid transportation in order to ensure an adequately large volume flow.

The removed lymph is then conveyed via the hollow chamber and the channel, which connects the hollow chamber to a low pressure-producing element, as a result of the effect of a suction force, to a sensor or sensor system. By means of such sensors or sensor systems, which are known per se, the concentrations of substances can be determined while the lymph is flowing past.

The invention also comprises the embodiment in which more than one hollow chamber is present in the form of an array.

A time of at least 5, preferably 10 to 60 minutes must be allowed for the formation of a sufficiently large liquid reservoir before the actual removal of the lymph should result.

It is a surprising result that, even at a later time, lymph can be removed continuously and over a longer time of many hours up to days.

The concentration determination can however also be effected after a time delay if the lymph is not measured directly while flowing by the sensors or sensor systems but instead the lymph is stored in the meantime in a collection container and the determination of the concentration of substances is implemented after a time delay subsequent to the removal of the lymph.

One or more penetration elements can be configured on the device according to the invention. The possibility exists also however of disposing such a penetration element on the hollow chamber or within the hollow chamber or even if necessary by directing it through the contact opening in the direction of the skin. During penetration, the skin can be cut, punctured, squeezed, burst or sliced with such a penetration element.

This process can be implemented easily and completely without blood since, due to the formation of the reservoir, a large spacing is produced between the uppermost layers of skin, which are not supplied with blood, and the lower layers of skin which are supplied with blood.

Such a penetration element can for example be a blade, a lancet, a needle or also a pin. However the possibility exists of configuring the edge of the contact opening(s) correspondingly, as is intended to be explained in more detail subsequently in the description of the embodiments.

One contact opening or a plurality of contact openings should have an inner width in the range between 0.01 to 10 mm, preferably between 0.1 to 5 mm and particularly preferred 1 mm, the contact opening being able to have various geometries (round, oval, square). If a plurality of contact openings should be used, it is favourable to dispose these regularly, the contact openings being able to form then an array, for example a 3×3 arrangement and the individual contact openings being configured at a respectively identical spacing from each other.

It is advantageous in addition to use a dermatologically safe adhesive, which is known per se, said adhesive being applied on the contact surface at least in the region around the contact openings in order to secure the device according to the invention on the skin and to seal the contact opening(s) against liquid permeation. The adhesive can thereby cover the entire contact surface. It can however also suffice to seal merely the external edges of the contact surface with such a corresponding adhesive. In order to prepare and condition the surface of the skin for the implementation of the method according to the invention, the skin can be treated in advance with disinfecting, degreasing, cleaning and other agents.

For the formation of the liquid reservoir and for the transportation of the lymph, a pressure should be set and maintained within the hollow chamber which is in the range of 0.05 to 1 bar, preferably in the range of 0.1 to 0.5 bar, below environmental pressure. The removed lymph can then be transported with a volume flow of at least 0.01 µl/min due to the suction force effect conditioned by the low pressure in the direction of the low pressure-producing element.

With the solution according to the invention, the removal of lymph can be effected with considerably reduced inconvenience for the respective patient. The possibility exists of implementing the removal continuously and therefore of implementing also a continuous determination of the concentrations of substances, of course a discontinuous measurement of such an analytical concentration also being able to be implemented optionally.

Since the liquid removal is effected only after formation of a sufficiently large liquid reservoir, damage to deeper layers of skin is avoided in all cases, a corresponding configuration and arrangement of a penetration element also being able to have an assisting effect for this purpose. The removeable lymph is not limited to the region in which a perforation is effected but instead the removed lymph can come from a region which has at least the dimension of the contact opening(s), but is generally also larger since the pressure gradient produces a flow divergence of the lymph also over a longer period of time.

It is also possible to implement the production and the penetration of the lymph reservoir by means of a simple measuring technological device. For this purpose, the complex resistance between the penetration element and an electrode situated on the skin surface is measured. This electrode can be applied to the contact surface. If the forming liquid reservoir has not yet reached the penetration element, then the measurable electrical capacitance is a measure for the spacing between the skin surface and the penetration element. After contact and to a greater extent after penetration, the ohmic component of the complex resistor increases greatly. In this way the formation of the body interface and the beginning of the lymph conveyance can be monitored in a targeted fashion.

The device according to the invention is constructed simply at least with respect to the part which comes into direct contact with the patient and therefore can be made available in a cost-effective manner so that it is possible without problem as a disposable application.

The solution according to the invention is intended to be explained better subsequently with reference to embodiments and with general clarification.

Figure 2:
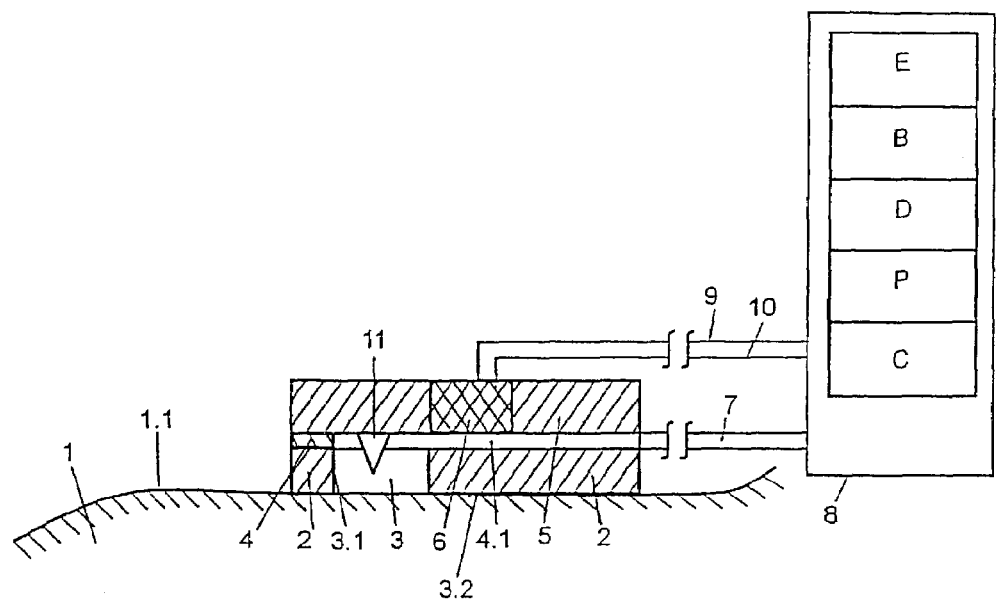
Figure 3:
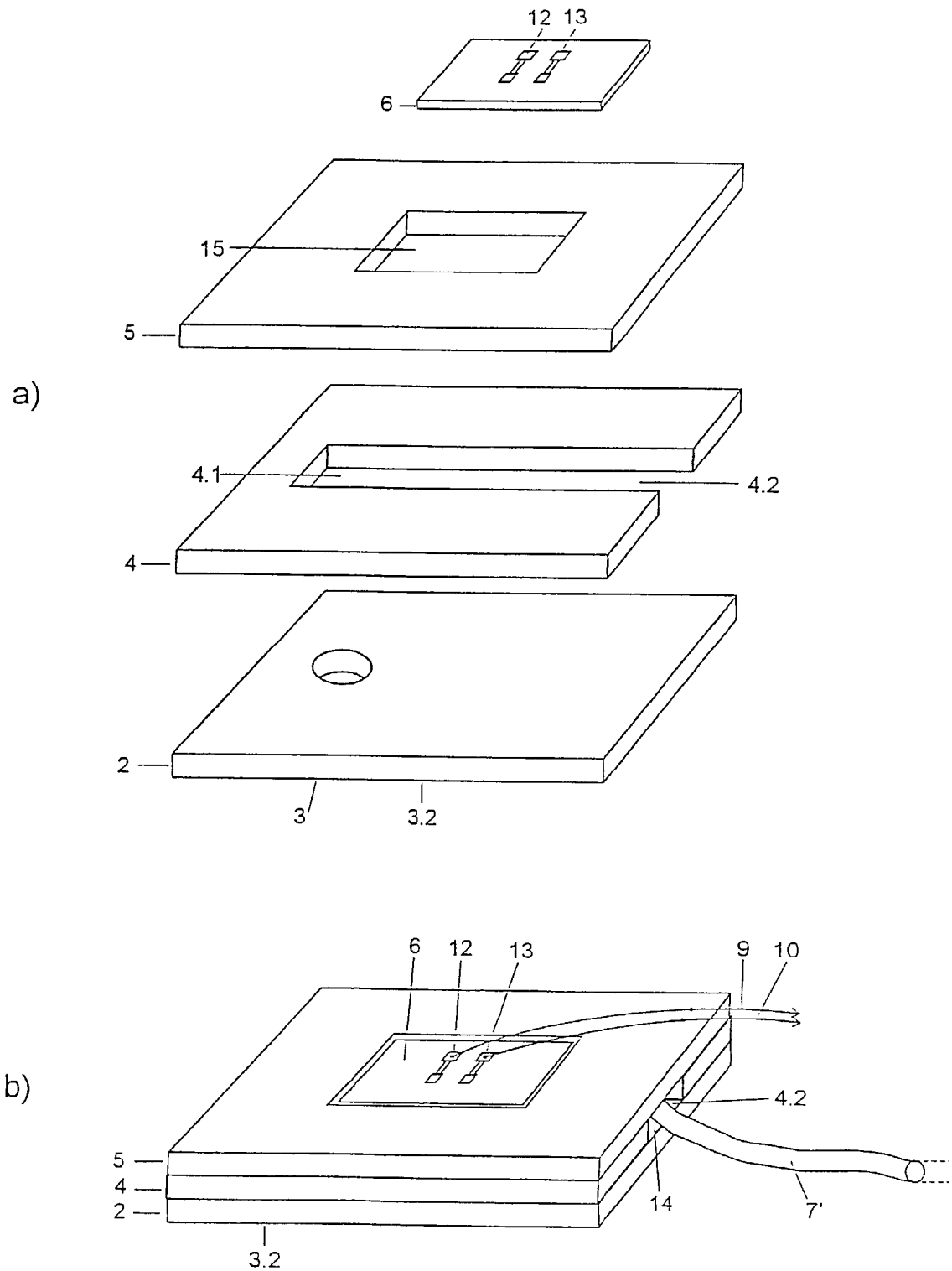
Figure 4:
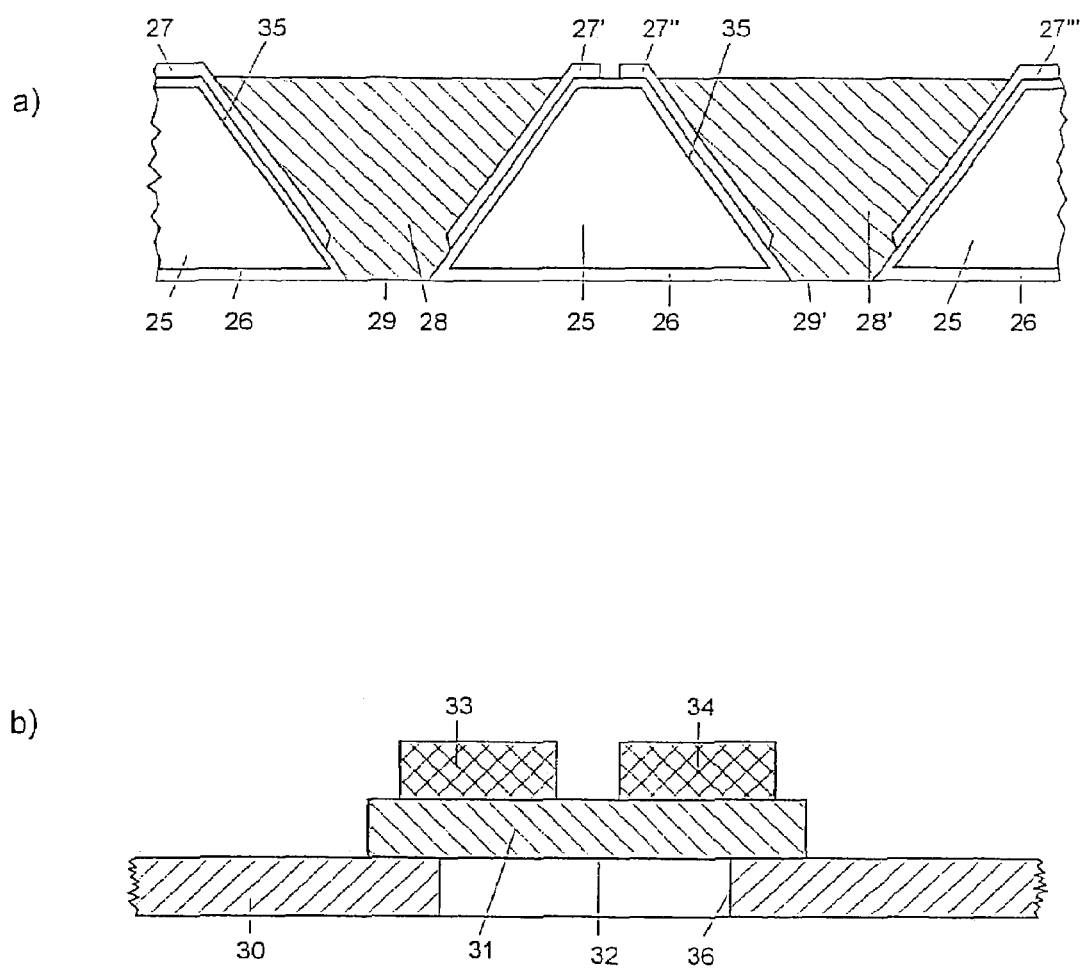
Figure 5:
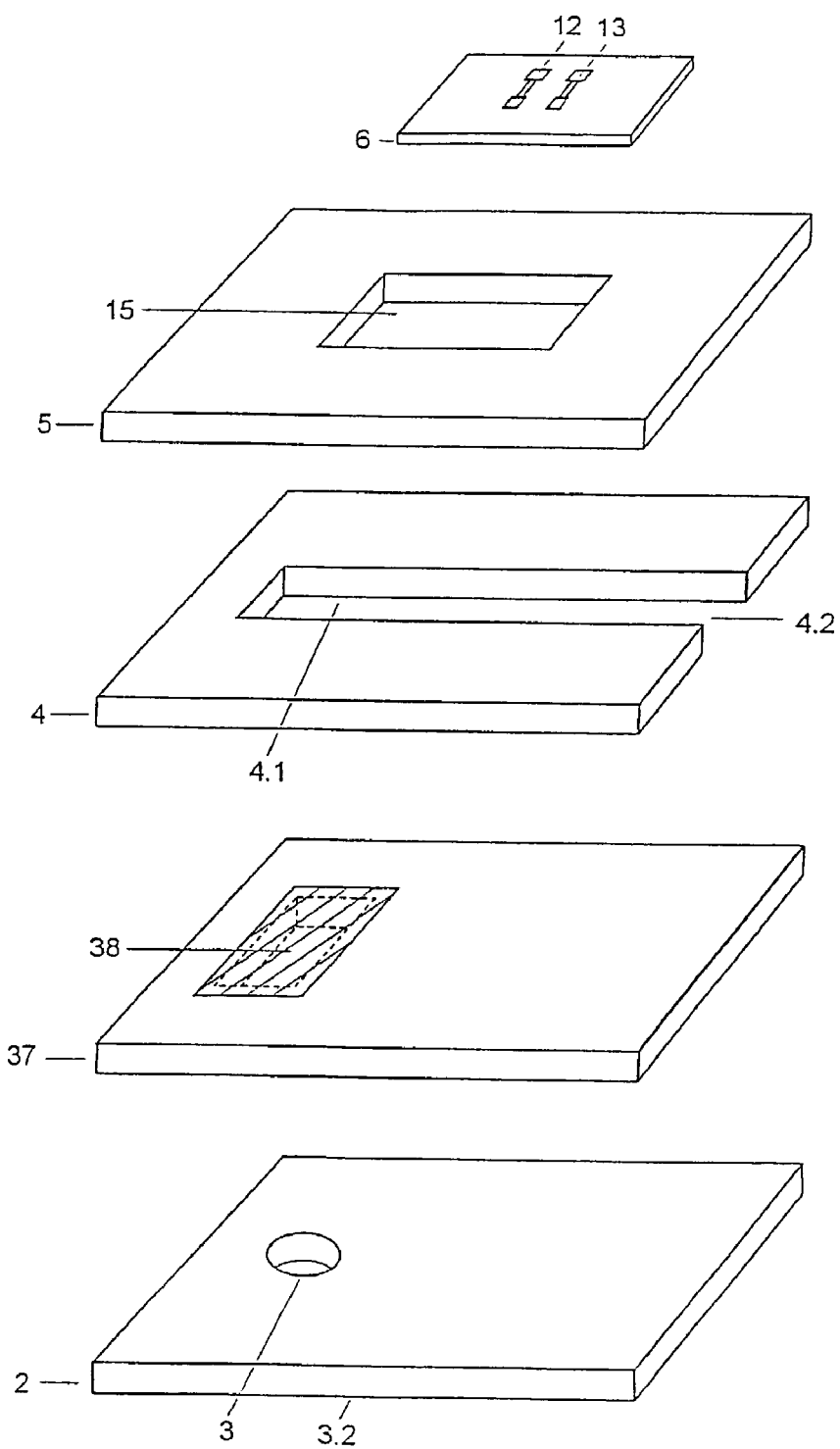
Figure 6:
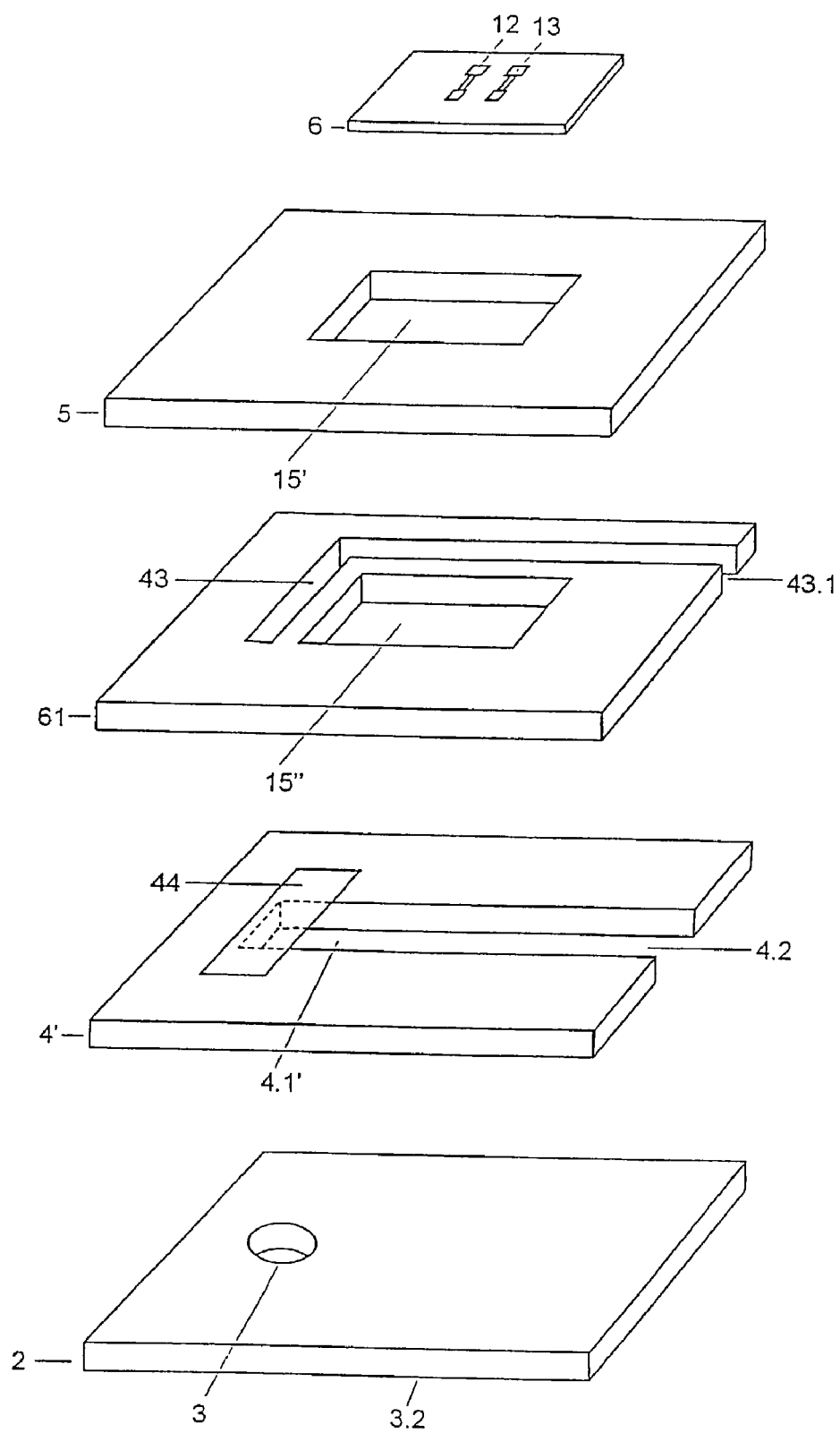
Figure 7:
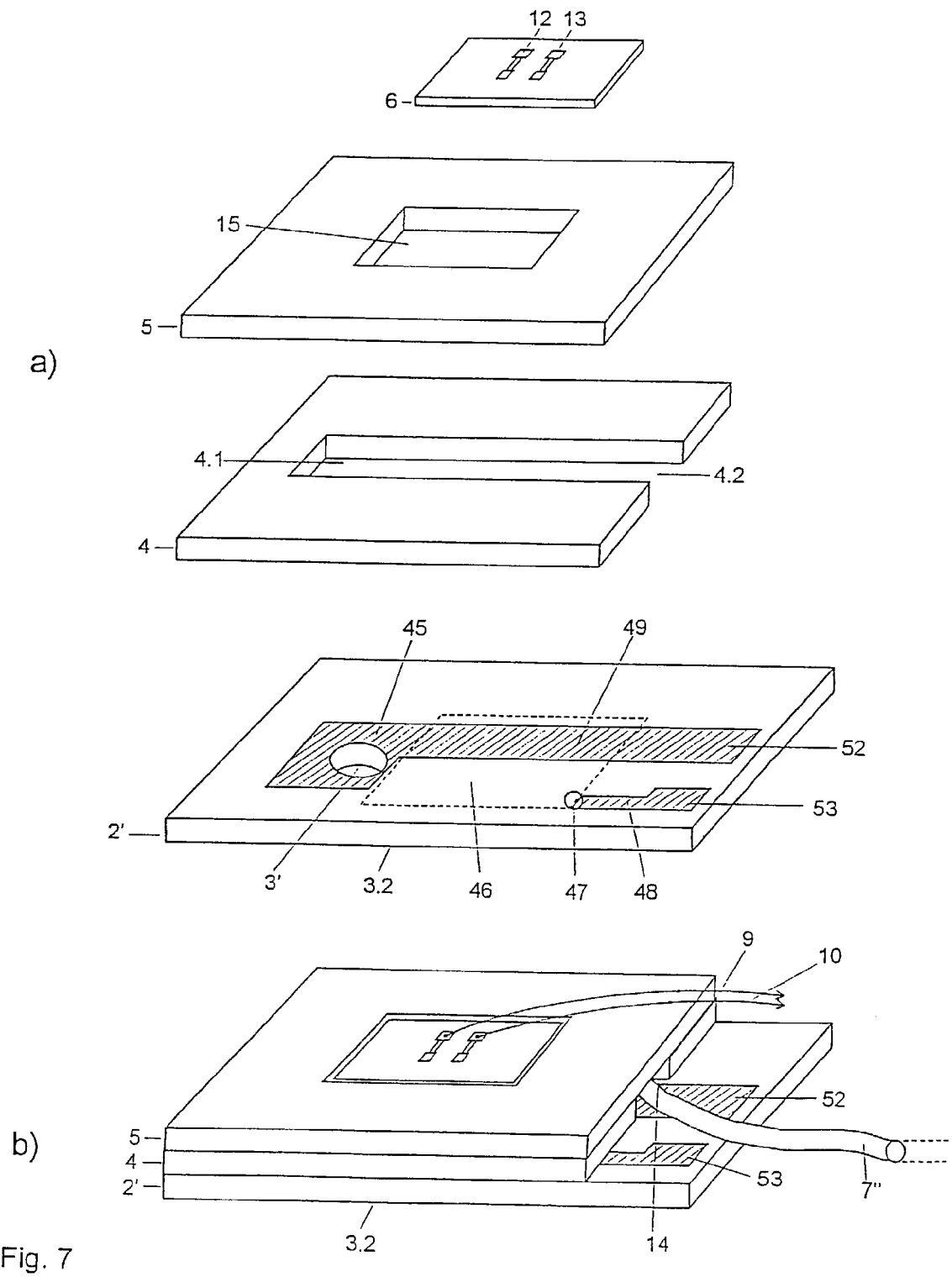
Figure 8:
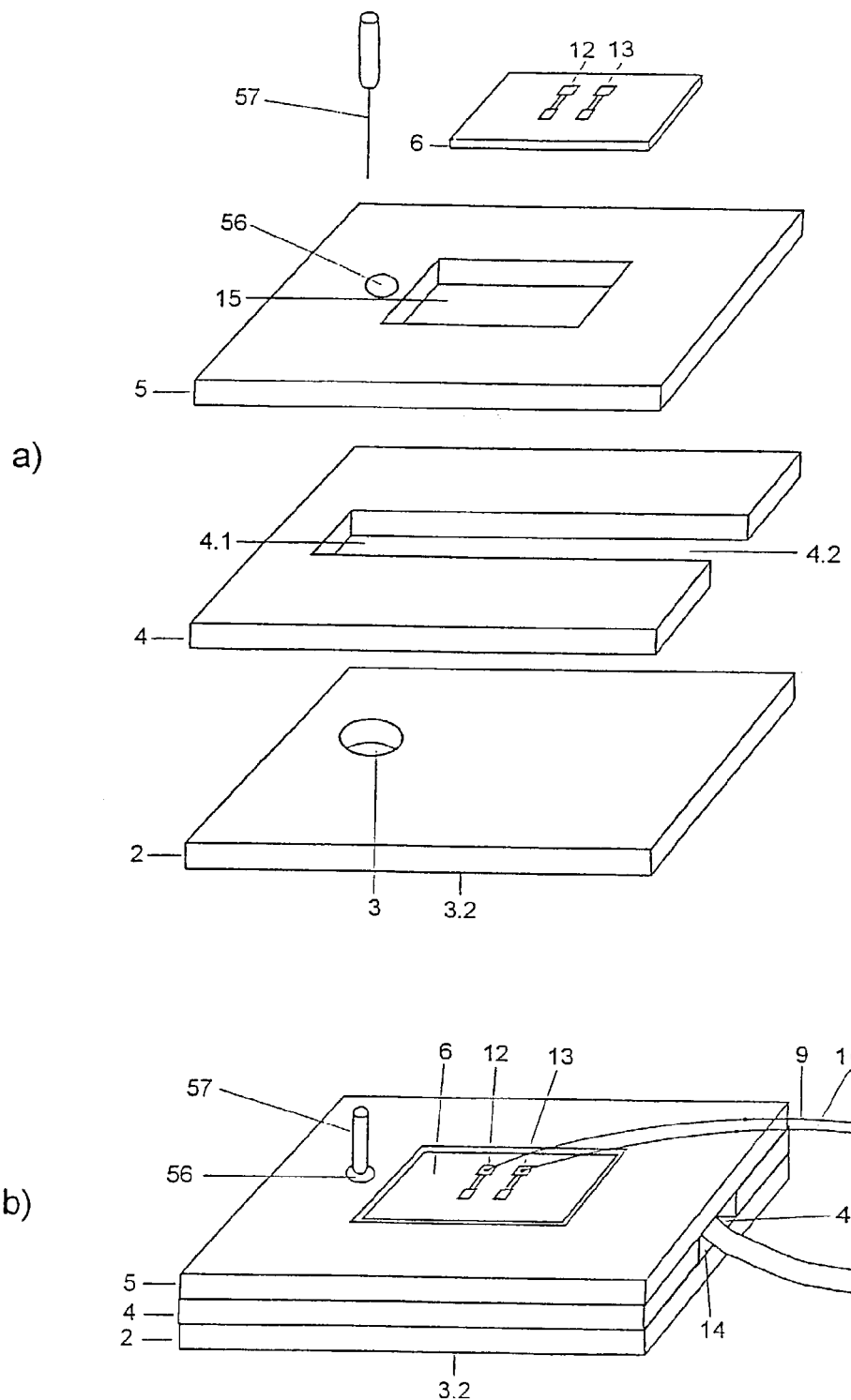
Figure 9:
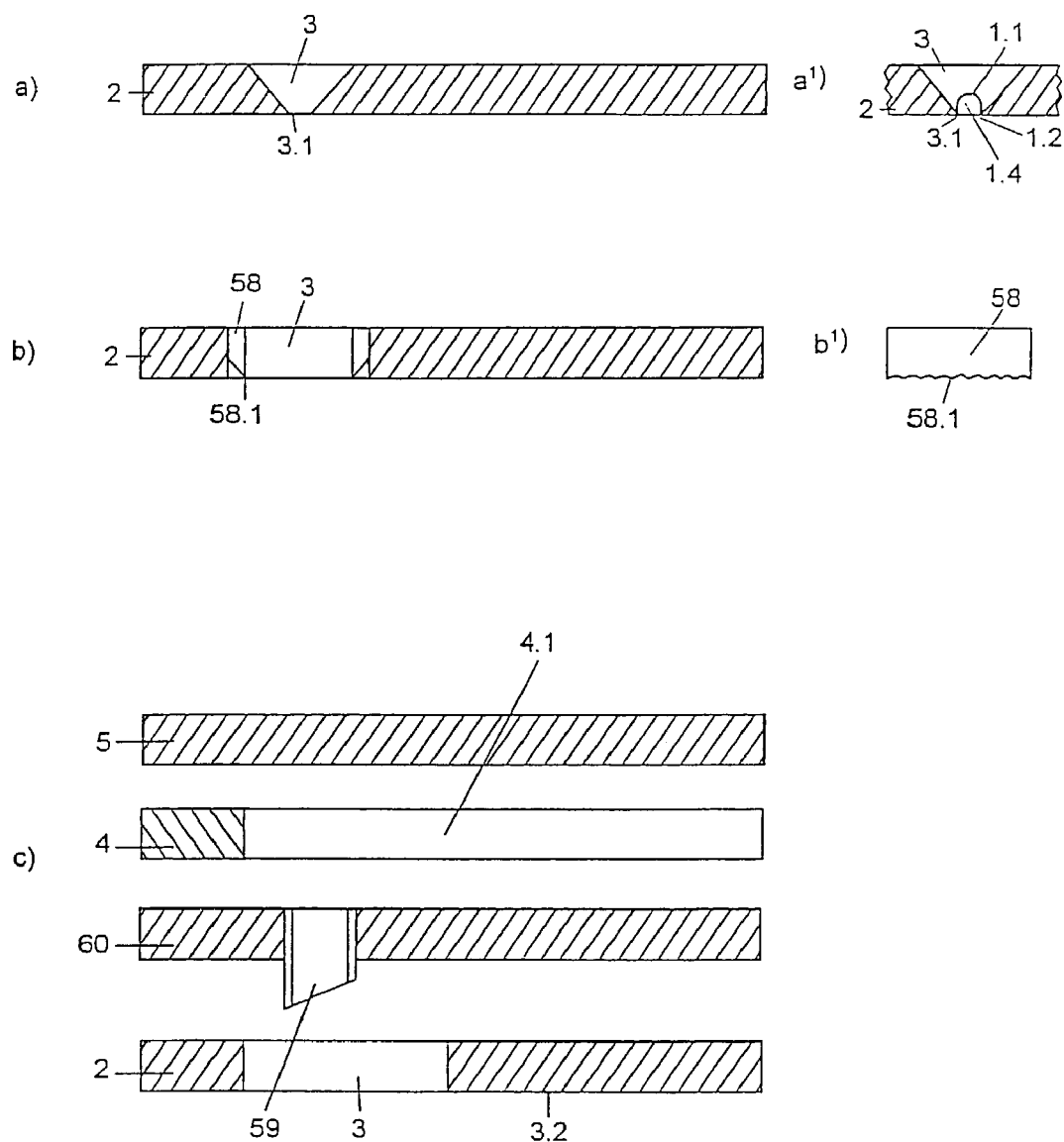
Figure 10:
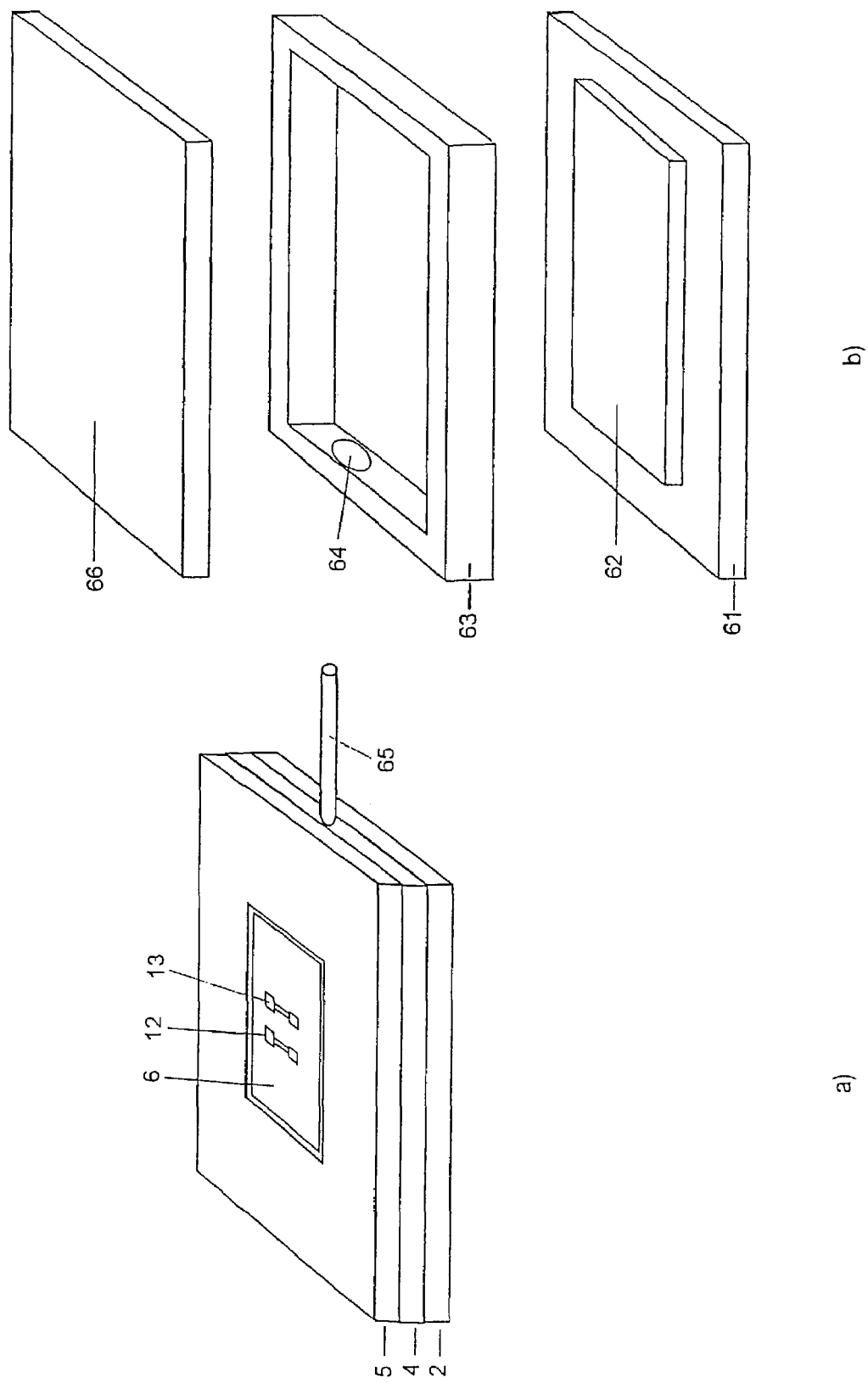
Figure 11:
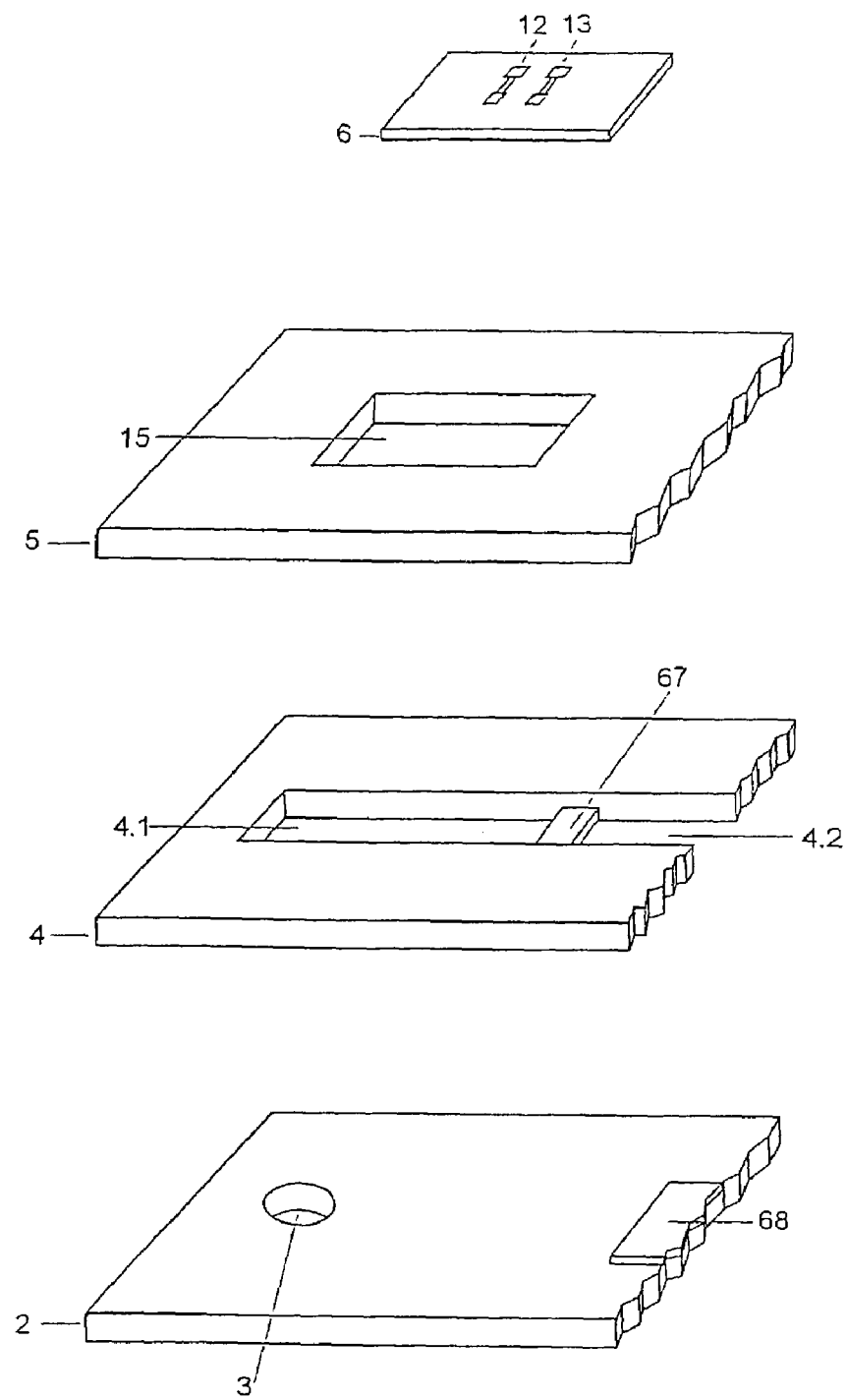

There are shown:

FIG. 1 in schematic form, taking into account physical regularities, the formation of a liquid reservoir within a skin layer system;

FIG. 2 an example of a device according to the invention in a section illustration;

FIG. 3 a further example of a device according to the invention;

FIG. 4 examples of suitable sensors;

FIG. 5 an example according to FIG. 3 with an additional filter membrane;

FIG. 6 an example according to FIG. 3 with an additional gas bubble trap;

FIG. 7 an example according to FIG. 3 with an electrode arrangement for producing an electro-osmotic liquid flow;

FIG. 8 an example according to FIG. 3 with an additional penetration element which can be introduced via a septum;

FIG. 9 examples of the arrangement and configuration of penetration elements on or in a contact opening;

FIG. 10 an example according to FIG. 3 with attached vacuum chamber and flow measuring device;

FIG. 11 an example according to FIG. 3 with integrated flow measuring device.

In FIG. 1, the formation of a liquid reservoir of lymph within the skin layer system is illustrated in schematic form. FIG. 1a) thereby shows the human skin 1 in a simplified section illustration. The layer sequence of the skin (cutis) of upper skin (epidermis) and dermis (corium) which are subdivided once again into stratum corneum, stratum lucidum, stratum granulosum, stratum spinosum, stratum basale, stratum papillare and stratum reticulare. Only the actual skin surface 1.1 and two further skin layers 1.2 and 1.3 are illustrated in a simplified form.

If now a low pressure is produced above the skin surface 1.1. via a here not-shown contact opening and the hollow chamber, then the result is a pressure gradient orientated perpendicularly to the skin surface as a result of gas permeability. This pressure gradient leads to a flow of lymph from the lower layers of the skin 1 perpendicularly to the skin surface 1.1. Since however the individual skin layers 1.1 to 1.3 are at varying degrees gas- and in particular liquid-permeable, this results in a flow divergence vector divJ. This fact has been made clear particularly in FIG. 1b). The vectorial dimension of the flow of the lymph vector $J_1$ points into the illustrated volume element (schematically for the self-forming liquid reservoir) whilst the vectorial dimension vector $J_2$ points out of the volume element. Since the upper skin layer 1.1. or the upper skin layers are permeable to a lesser degree for the lymph than those lying thereunder, the flow of lymph J is reduced in y-direction.

This implies that the divergence of the liquid density vector J is negative (vector divJ<0). Vector $J_2$ is illustrated greatly exaggerated in FIG. 1b) and in fact vector $J_2$ tends to 0.

Since more lymph is supplied to the volume element than is discharged, the result is formation of a mechanical stress between the layers of skin. This leads after a few minutes (in general 10 to 60 min) to a separation of the individual layers of skin so that a liquid reservoir, which is filled with lymph, is formed between the layers of skin. Such a liquid reservoir 1.4 is shown in FIG. 1c).

The removal of the lymph can be assisted or achieved if the uppermost skin layer 1.1 is slightly perforated also above the liquid reservoir 1.4. Since the low pressure can act further, it is possible to remove the lymph from the liquid reservoir 1.4 and to transport it further in the direction of a low pressure-producing element, which is likewise not shown here. Lymph can also be removed continuously at a later time since the uppermost skin layer, after perforation, does not represent a barrier for the flow.

In FIG. 2, a section illustration of an example of a device according to the invention is shown with a connected system unit 8.

The device is placed by its contact surface 3.2 on the surface of the skin 1.1 on which the contact surface 3.2 with the contact opening 3.1 is situated. The hollow chamber 3 is connected via a channel 4.1 and a thereto connected line 7 to the system unit 8. In the system unit 8, a vacuum pump P is present as a possible low pressure-producing element with which a corresponding low pressure can be set via the line 7 in the channel 4.1 and in the hollow chamber 3.

Subsequent to the hollow chamber 3, a sensor 6 for determining the concentrations of substances is disposed on the channel 4.1. The removed lymph is transported along its sensitive surface regions as a result of a suction force effect.

By means of the sensor 6, at least one substance component which is contained in the lymph can be measured.

The lymph can then be guided further into a container C, which likewise is integrated into the system unit 8, and be securely stored there.

The sensor 6 is connected via lines 9 and 10 to a measuring electronic unit E which likewise is a component of the system unit 8. The correspondingly processing measurement results can then be read into a memory which is likewise integrated there or be issued to a further evaluation device via a data transfer electronic unit D.

In the system unit 8, there can in addition be an electrical energy supply, for example an accumulator B, which makes available the required electrical energy for the sensor 6, the measuring electronic unit E, the data transfer electronic unit D or the vacuum pump P.

In the hollow chamber 3 there is a penetration element, for example a pin 11 available, the front tip of which as shown has no contact with the skin surface 1.1 before formation of the liquid reservoir 1.4.

As a result of the low pressure effect and the formation of the liquid reservoir 1.4, the result can be, after a corresponding time, that the skin surface arches up to the tip of the pin 11 and the uppermost skin layer 1.1 is perforated at this contact point and the lymph is removed from the liquid reservoir by the perforation, is transported via the channel 4.1 to the sensor 6 and into the collection container C. The penetration element 11 can protrude for example also sideways into the hollow chamber 3.

The low pressure can, as already described in the general part of the description, be maintained also over a longer period of time so that lymph can be further removed also continuously for the determination of the concentrations of substances since the uppermost skin layer no longer represents a barrier for the flow after the perforation.

The pin 11 as penetration element can however also be configured in the form of a blade, lancet or also as a needle.

In FIG. 3, a further example of a device according to the invention is shown in an exploded and in a perspective illustration.

In FIG. 3a), individual elements, from which such a device can be formed, are detectable. These elements have a plate-shaped configuration but can also be used as films and represent a carrier 2 with a contact surface 3.2 which is present on the skin side. A hollow chamber 3 is configured in the carrier 2. A channel carrier 4 is placed on the carrier 2, the channel 4.1 of which communicates with the hollow chamber 3. The channel 4.1 discharges into a channel opening 4.2 externally.

A plate-shaped cover 5 can be placed on the channel carrier 4, in which cover an opening 15 is configured. A sensor 6 with non-illustrated active membrane surfaces can be inserted into the opening 15, on which sensor contact surfaces 12 and 13 are present on the outside, from which the electrical signals can be conducted via flexible lines 9 and 10 to a measuring electronic unit.

The sensor 6 is disposed in the cover such that the corresponding electrodes, i.e. the sensitive part for measurement of the concentrations of substances are disposed in the region of channel 4.1 and the removed lymph which is transported as a result of the suction force effect can be guided past the active membrane surfaces.

As flexible a line 7 as possible can be introduced into the channel opening 4.2. and be sealed tightly with a seal 14 so that the removed and conveyed lymph can pass through the flexible line 7 into a collection container C and at the same time the low pressure in the hollow chamber 3 and in the channel 4.1 can be set via the flexible line 7.

The three plate-shaped elements, namely the carrier 2, the channel carrier 4 and the cover 5 can be connected to each other by the most varied of methods, the connection being intended however to be liquid-impermeable.

A sensor element is illustrated in FIG. 4a), as already described in DE 41 15 414 A1. It is intended herewith to make reference expressly to the disclosure content of this patent application.

Such a sensor element comprises a silicon carrier 25 which has on its surface a dielectric layer 26 made of $SiO_2$ and/or $Si_3N_4$.

Truncated pyramid-shaped openings, as so-called containments 35, are formed in this silicon carrier 25, for example by anisotropic etching. The downwardly tapering containments 35 are provided with electrode layers, 27, 27', 27'', 27''' on internal surfaces which are inclined towards and opposite each other, the electrode layers being made for example of platinum or Ag/AgCl or representing a corresponding cover layer.

A membrane material 28, which is made for example of PVA and is filled with the enzyme glucose oxidase (GOD) (operating electrode) is received in a containment 35 with electrode layers 27, 27', which are made for example of platinum. A membrane material 28, which is made for example of PVA (reference electrode) is received in a second containment 35 with electrode layers 27'', 27''', which are made for example of Ag/AgCl. On the lower tapered side, the membrane 28, 28' is located freely and forms active membrane surfaces 29, 29' which are in contact with the removed lymph and correspondingly are in contact with the lymph transported correspondingly through the channel 4.1.

On the electrodes 27, 27', 27" and 27'" configured as layers, the electrically conductive connection lines 9 and 10 are directly contacted so that they can take over the function of the contact elements 12 and 13, as shown in FIG. 13.

A sensor element is shown in FIG. 4*b*), as has been described already in DE 41 37 261 C2, and the entire content here is intended to go back to its content.

An opening 36 is configured on a sensor element carrier 30, above which opening a double matrix membrane 31 is placed. The double matrix membrane 31 can be made for example of a paper, which is soaked with a gel which contains the enzyme glucose oxidase (GOD). Two electrodes 33 and 34 are applied on the double matrix membrane 31, for example by known evaporation coating methods or in screen printing technology. The electrode 33 is thereby made of platinum and the electrode 34 of Ag/AgCl. The electrodes 33 and 34 are at a spacing from each other and are electrically separated.

An active free membrane surface 32 in the opening 36 forms the upper end of the channel 4.1 so that the lymph has direct contact here also.

The electrical voltage can also be directly tapped by the electrodes 33 and 34 so that they can likewise take over the function of the sensor contact surfaces 12, 13 according to the example of FIG. 3.

Of course, other sensor elements can also be used in addition to the sensor elements described here which, with a corresponding arrangement with respect to the channel 4.1, can also measure concentrations of substances of other components. In addition to electrochemical sensors, this applies also for optical, for example polarimetric sensors which can be used if the channel 4.1 is configured as a cuvette.

Furthermore, temperature sensors and sensors for the flow of the lymph and for other parameters can also be integrated in the channel 4.1.

The example shown in FIG. 5 of a device according to the invention is modified relative to the example according to FIG. 3 in as much as a membrane 38 is disposed between the hollow chamber 3 and the channel 4.1. The membrane 38 has the task of filtering the lymph. In this example, an additional membrane carrier 37 with the membrane 38 is used which is disposed between the carrier 2 and the channel carrier 4 and is connected to the latter. In the case of suitable membrane materials, such a membrane carrier 37 can however also be dispensed with.

The example illustrated in FIG. 6 has been supplemented with a so-called gas bubble trap, relative to the example according to FIG. 3. For this purpose, an additional channel 43 is present, between which channel and the hollow chamber 3, a gas permeable membrane 44 (for example PTFE, silicone) is disposed. After the removal of the lymph, the gas components possibly contained therein penetrate through the gas permeable membrane 44 and are discharged externally via the channel 43. The liquid components of the lymph, as described already, are guided into the channel 4.1 and the respective concentration of substances is determined by means of the sensor 6.

In this example, an addition channel carrier 61 has been used which has been disposed between the channel carrier 4 and the cover 5. In addition, a further opening 15' is configured in this channel carrier 61, into which opening the sensor 6 can be inserted.

The channel 43 discharges into a separate channel opening 43.1 to which in turn a low pressure can be applied so that the removed and correspondingly transported lymph can be degassed even more effectively.

In order to produce the corresponding low pressure in the channel 43, a separate pump can be used as low pressure-producing element, but the possibility also exists of placing a corresponding bypass with which it is possible to use a single low pressure-producing element.

Due to the lymph passing by the sensor 6 now being bubble-free, measurement errors can be further avoided or greatly reduced.

By using the known principle of electro-osmosis, the removal and the transportation of the lymph can be assisted.

A correspondingly modified device is illustrated in FIG. 7 and is described at least in a similar form in the unpublished German Patent application DE 198 48 112.

Additional electrodes 52 and 53 for producing an electro-osmotic flow are thereby configured as layers on the contact surface 3.2 and the surface of the carrier 2.

On the surface of the carrier 2, a metal layer 45 is configured around the hollow chamber 3 and possibly also on the internal wall of the hollow chamber 3, which metal layer is connected via a conductive track 49 to the electrical contact 52.

A further contact surface 46 is present on the underside of the carrier 2 and is connected via a feedthrough 47 to a further conductive track 48 which leads to a second electrical connection contact 53. An electrical voltage can be applied via the contacts 52 and 53 so that the contact surface 46 is connected as anode and the contact surface 45 as cathode. The contact surface 46 is hereby located in direct contact with the skin surface 1.1. The electrode layer 45 is in direct contact with the removed and transported lymph.

Because of the voltage difference between the anode and cathode, an electro-osmotic flow of lymph is initiated in the skin and the removable and transportable volume flow can be correspondingly increased.

For the various electrodes, conductive tracks and the contacts, for example platinum can be used but also other electrically conductive materials, such as for example screen printing pastes. These elements can also be applied in addition to the screen printing with other methods known from thin layer technology.

In FIG. 8, an example of a device according to the invention according to FIG. 3 is shown in which a penetration element 57, for example a needle, is guided through the hollow chamber 3 onto the skin surface 1.1 and thus the skin surface 1.1 can be penetrated. A septum 56 is thereby introduced in the cover 5 above the hollow chamber 3, through which the needle-shaped penetration element 57 can be introduced and, because of the corresponding arrangement and dimensioning of the channel 4.1, can be directed through the hollow chamber 3 onto the skin surface 1.1.

In FIG. 9, possible examples of the configuration of the penetration elements directly on the contact openings 3.1 or within a hollow chamber 3 are illustrated.

In FIG. 9*a*), a hollow chamber 3 is illustrated which tapers conically in the direction of the contact surface 3.2, in which hollow chamber the available contact opening 3.1 is correspondingly smaller so that, at the edge of the contact opening 3.1, a correspondingly larger force is in effect. The contact opening 3 thereby forms a sharp edge. In the right-hand illustration of FIG. 9*a*), there is shown how the liquid reservoir 1.4 arches up and protrudes even into the inside of the hollow chamber 3. The penetration of the upper skin layer 1.1 is achieved with the sharp edges of the contact opening 3.1.

In the example according to FIG. 9b), a penetration insert 58 is inserted into the hollow chamber 3, which is per se configured cylindrically, and abuts against the external edges of the hollow chamber 3.

The end face of this penetration insert 58 pointing in the direction of the contact surface 3.2 is chamfered and forms the sharp edge 58.1 similarly to that of a knife or a blade, which does not however protrude beyond the contact surface 3.2 and the skin surface 1.1 is only penetrated after formation of a sufficiently large liquid reservoir 1.4. In the right-hand illustration of FIG. 9b), a toothed or undulating configuration of the sharp edge 58.1 can be detected which can be used optionally. The penetration insert 58 can also be inserted into the contact opening such that the sharp edge 58.1 has a spacing of for example 2 mm from the lower edge of the hollow chamber 3.

Such a penetration insert 58 can be made of various materials, such as metal, ceramics or a plastic material and can be adapted in its external and internal contour to the shape used for the hollow chamber 3.

In the example according to FIG. 9c), an additional penetration carrier 60 is used which is disposed between the carrier 2 and the channel carrier 4, on which penetration carrier a hollow cannula 59 is configured in the inside and is disposed such that it is guided through the hollow chamber 3 for the penetration of the upper skin layer 1.1. The lymph can pass through the interior of this cannula 59 into the channel 4.1 and from there be transported to the sensor 6 (not illustrated here).

A device according to FIG. 3b) is illustrated in FIG. 10a. Instead of the flexible line 7, a cannula 65 is used here. This cannula 65 can be introduced into a vacuum chamber which is shown in FIG. 10b as an exploded drawing. A base plate 61 is connected securely to a frame 63 and sealed firmly with a cover plate 66. A septum 64 is inserted in the frame 63. After the production, the air is withdrawn from the chamber for example via the septum 64. For the operation of the device according to the invention, the parts from FIGS. 10a and 10b are combined such that the cannula 65 penetrates the septum 64. Both parts can be connected securely and unalterably by means of a mechanical device which is not shown (for example according to the click-in method). In this manner, a unit is formed from a device according to FIG. 3b and a vacuum chamber which can replace a conventional vacuum pump or a vacutainer known in medical technology. It is thereby also possible to give the vacuum chamber a larger dimension than is illustrated in FIG. 10. A plurality of vacuum chambers can then also be stacked. It is also possible to manufacture the vacuum chamber from thin flexible films which are adapted during application to the body of the patient. In order that the vacuum chamber cannot be compressed due to the external air pressure, spacers (not illustrated) can also be inserted between the base plate 61 and cover plate 66.

One or more capillary bodies 62, for example a fleece, can be disposed also in the vacuum chamber, said fleece absorbing the lymph because of its capillary forces. The capillary body or bodies 62 can be securely connected to the base plate and/or cover plate.

A simple possibility for checking the lymph flow resides in counting the drops emanating from the cannula 65 per unit of time, if they have become so large that they touch the capillary body 62 and are removed by suction because of the capillary forces. This can occur for example in an electrical manner in that the electrical resistance between the cannula and a flat electrode layer (not shown), which is disposed between the capillary body 62 and the base plate 61 and/or cover plate 66, is measured.

A further possibility for integration of a flow control is shown in connection with FIG. 3 in FIG. 11. Here the plate-shaped elements are illustrated on the right-hand side, broken off. A direct transition into a vacuum chamber can be effected here for example as is described in FIG. 10b. In this case a septum 64 would be omitted. A narrowing point 67 is introduced in the channel 4.1. A capillary body 68 is firmly connected to the carrier 2, which body leads on the right into the non-illustrated vacuum chamber and is able to fill the latter in part.

The flow of lymph can also be monitored or checked here in that the liquid drops per unit of time which emerge after the channel narrowing 67 are counted. Because of the small spacing between the channel narrowing 67 and the capillary body 68, the drop can only grow for a short time until it touches the capillary body 68 and is removed by suction. The electrical measurement is effected here also by measurement of the electrical resistance between two electrodes which are disposed for example at the narrowing point 67 and between the capillary body 68 and the carrier 2 (not shown).

In order to monitor or to check the transportation or the flow of the lymph, the possibility also exists of arranging on a sensor 6 two or more glucose sensors one behind the other on the channel 4.1 in the flow direction. Due to the relatively small volume flows and flow velocities, the result is glucose consumption in the channel 4.1. This consumption is reflected in a reducing measurement signal on the respectively subsequent glucose sensor.

Simply by comparing the measurement results of the sensors disposed one after another, it can be monitored therefore whether a lymph transportation is being effected or not.

The plate-shaped elements shown and described in the examples, such as the carrier 2, the channel carrier 4, the cover 5 and the other carriers can be made of suitable plastic materials, such as polyvinyl chloride, polyethylene, polyoxymethylene, polycarbonate, ethylene/polypropylene COP, polyvinylidene chloride, polychlorotrifluoroethylene, polyvinyl butyral, cellulose acetate, polypropylene, polymethylmethacrylate, polyamide, tetrafluoroethylene/hexafluoropropylene COP, polytetrafluoroethylene, vinyl formaldehyde, epoxide, polyurethane, polyester, silicone, melamine-formaldehyde, urea-formaldehyde, aniline-formaldehyde, capton or other plastic materials.

The connecting of these plate-shaped elements can be effected by adhesion, welding or laminating. Laminating films which can be hot-laminated are available in particular for lamination. Such a suitable film is a so-called CODOR film made of polyethylene and polyester which is commercially available from the company TEAM CODOR, Marl, Federal Republic of Germany.

The thickness of these plate-shaped elements can be between 10 and a few 1000 μm. For the plate-shaped element 2, the thickness is preferably a few mm and for the other plate-shaped elements a few 100 μm.

The flat extension of the plate-shaped elements can be chosen in the range of a few $cm^2$, thus for example the contact surface 3.2 can be dimensioned with the dimensions 1 cm×2 cm, at least the carrier 2 achieving a corresponding dimension. A dermatologically safe adhesive material can be present on the contact surface 3.2, as already mentioned in the general part of the description, which ensures reliable adhesion on the skin surface and the required sealing. Suitable adhesive materials are known in medical dressings technology.

The individual plate-shaped elements, but also the entire device can however be produced also in the injection moulding method in which at the same time the hollow chamber 3, the channel 4.1 and the opening 15, into which the sensor 6 is insertable, can be produced already during manufacture.

Deviating from the illustrated and described embodiments, the penetration elements can however also be disposed and secured on other plate-shaped elements, other geometric shapes also being readily possible.

Instead of a pump device or a vacuum pump, a so-called "vacutainer" can also be used which is known in medical technology and is commercially and cheaply available, which "vacutainer" can be connected correspondingly to the channel 4.1 and the hollow chamber 3. As a result, the complexity in producing the required low pressure can be further reduced. This is reflected not only in a reduced price but also increases the possible mobility of such a device since the electric energy required for the operation can be substantially reduced and electric energy is required merely for the implementation and accomplishment of the measurement.

Instead of using one device, it is also possible to use devices using two parts in which the function of production and penetration of a reservoir and the continuous conveyance and measurement of different parameters of the lymph are separated. Initially a device with a first part is hereby placed on the skin and a low pressure is produced. After the start of the lymph flow, the first part can be replaced by exchanging with a second part of the device having the integrated sensor device. This second part of the device can also be operated without low pressure-producing elements, such as vacuum pump or vacutainer, if the hollow space 3, channel 4.1 and container for the collection of lymph is filled with a capillary body which can convey the liquid flow over a long time because of the capillary forces.

Advantageously, a common carrier can be used for both parts of the devices which remains on the skin surface while changing the devices. The placing and fixing of the devices on the carrier can be effected by mechanical means according to the "click-in" method.

What is claimed is:

1. A method for removing liquid from endogenic tissue and determining concentrations of substances in this liquid, comprising:
    placing a device on a skin surface, the device having at least one contact opening configured on at least one hollow chamber in a contact surface,
    setting a low pressure at the hollow chamber and, forming a liquid reservoir underneath the skin surface,
    collecting the liquid in the liquid reservoir,
    subsequently flowing the liquid from the liquid reservoir out of the tissue and guiding the liquid with suction forces occasioned by low pressure to a sensor or a sensor system, which is disposed on the channel or is integrated in the wall of the hollow chamber, and
    monitoring a lymph flow by determining the number of drops per unit of time, which are sucked into a capillary body.

2. The method according to claim 1, comprising setting a pressure in the hollow chamber, which is 0.05 to 1 bar below the ambient pressure, for the formation of the liquid reservoir and the transportation of the liquid.

3. The method according to claim 1, comprising transporting the liquid with a volume flow of at least 0.01 $\mu$l/min to the sensor or to the sensor system.

4. The method according to claim 1, comprising continually conveying the liquid.

5. The method according to claim 1, further comprising penetrating at least an uppermost skin layer lying above the liquid reservoir after formation of the liquid reservoir with the help of a penetration element disposed in the hollow chamber or guidable through the contact opening of the hollow chamber in the direction of the skin.

6. A device for removing liquid from endogenic tissue and determining concentrations of substances in this liquid, comprising:
    at least one hollow chamber having at least one contact opening disposed on a contact surface, the hollow chamber being placeable in direct contact on the skin covering the tissue, and the hollow chamber being connected to a low pressure-producing element via a channel, and
    a sensor or sensor system disposed on the channel, and/or a sensor or sensor system being integratable into a wall of the hollow chamber;
    wherein the device comprises two parts, wherein one part is present with an element producing low pressure and a second part is present with at least one sensor; and
    wherein both parts are interchangeable.

7. The device according to claim 6, wherein the sensor or the sensor system is disposed on the device such that it is in contact with the liquid.

8. The device according to claim 6, wherein the contact opening has an inner width of from 0.01 to 10 mm.

9. The device according to claim 6, further comprising a penetration element disposed on the hollow chamber in the direction of the skin.

10. The device according to claim 9, wherein the penetration element comprises at least a blade, a lancet, a needle, or a pin.

11. The device according to claim 9, wherein the contact opening includes an external edge, the external edge of the contact opening being configured as a second penetration element.

12. The device according to claim 6, wherein the contact opening is surrounded in a liquid-impermeable manner when placed in position on the skin.

13. The device according to claim 6, further comprising an adhesive, the adhesive being applied at least around the contact opening on the contact surface, and/or on other external edges.

14. The device according to claim 6, including a plurality of sensors or sensor systems, the plurality of sensors or sensor systems being disposed one behind the other in a transportation direction of the liquid.

15. The device according to claim 6, further comprising a membrane, the membrane being disposed between the hollow chamber and the channel.

16. The device according to claim 6, wherein the low pressure-producing element comprises at least a vacuum chamber.

17. The device according to claim 6, wherein at least one capillary body is disposed in the vacuum chamber, in or connected to the channel.

18. The device according to claim 6, wherein a membrane is disposed between electrodes and which are separated from each other, said membrane separating the electrodes from the liquid transported through the channel.

19. The device according to claim 6, wherein electrodes for the sensor or sensor system are formed from platinum or Ag/AgCl.

20. A device for removing liquid from endogenic tissue and determining concentrations of substances in this liquid, comprising:
at least one hollow chamber having at least one contact opening disposed on a contact surface, the hollow chamber being placeable in direct contact on the skin covering the tissue, and the hollow chamber being connected to a low pressure-producing element via a first channel, and a penetration element disposed in the hollow chamber in the direction of the skin,
a gas-permeable membrane and a further channel, the gas-permeable membrane being disposed between the hollow chamber and the further channel, the further channel being connected to the low pressure-producing element,
wherein
a sensor or a sensor system is disposed on the first channel.

21. A device for removing liquid from endogenic tissue and determining concentrations of substances in this liquid, comprising:
at least one hollow chamber having at least one contact opening disposed on a contact surface, the hollow chamber being placeable in direct contact on the skin covering the tissue, and the hollow chamber being connected to a low pressure-producing element via a channel, and a penetration element disposed in the hollow chamber in the direction of the skin,
wherein
a sensor or a sensor system is disposed on the channel, and wherein a plurality of contact openings is present on one or more hollow chambers.

22. A device for removing liquid from endogenic tissue and determining concentrations of substances in this liquid, comprising:
at least one hollow chamber having at least one contact opening disposed on a contact surface, the hollow chamber being placeable in direct contact on the skin covering the tissue, and the hollow chamber being connected to a low pressure-producing element via a channel, and a penetration element disposed in the hollow chamber in the direction of the skin,
an anode and a cathode, the anode being adapted for contact with skin and the cathode being adapted for contact with a lymph, the anode and the cathode being configured on the contact surface,
wherein
a sensor or a sensor system is disposed on the channel.

23. A device for removing liquid from endogenic tissue and determining concentrations of substances in this liquid, comprising:
at least one hollow chamber having at least one contact opening disposed on a contact surface, the hollow chamber being placeable in direct contact on the skin covering the tissue, and the hollow chamber being connected to a low pressure-producing element via a channel, and a penetration element disposed in the hollow chamber in the direction of the skin,
wherein
a sensor or a sensor system is disposed on the channel, and wherein the device is formed from a plurality of plate-shaped elements, which are connected to each other, and the hollow chamber and the channel are configured and a plate-shaped element is the carrier of the sensor or of the sensor system.

24. A device for removing liquid from endogenic tissue and determining concentrations of substances in this liquid, comprising:
at least one hollow chamber having at least one contact opening disposed on a contact surface, the hollow chamber being placeable in direct contact on the skin covering the tissue, and the hollow chamber being connected to a low pressure-producing element via a channel, and a penetration element disposed in the hollow chamber in the direction of the skin,
wherein
a sensor or a sensor system is disposed on the channel, and wherein the sensor system is configured as a plate-shaped element in which at least one containment is introduced, the containment tapering from the surface of the plate-shaped element in the direction of a surface oriented towards the channel, an oppositely-situated surface in which the containment is coated with electrodes and, in the containments, a membrane material is contained, the membrane surfaces of which, oriented in the direction of the channel, are in contact with the liquid transported through the channel.

25. A device for removing liquid from endogenic tissue and determining concentrations of substances in this liquid, comprising:
at least one hollow chamber having at least one contact opening disposed on a contact surface, the hollow chamber being placeable in direct contact on the skin covering the tissue, and the hollow chamber being connected to a low pressure-producing element via a channel, and a penetration element disposed in the hollow chamber in the direction of the skin,
wherein
a sensor or a sensor system is disposed on the channel, and wherein the device determines glucose concentrations in the lymph of humans.

26. A device for removing liquid from endogenic tissue and determining concentrations of substances in this liquid, comprising:
at least one hollow chamber having at least one contact opening disposed on a contact surface, the hollow chamber being placeable in direct contact on the skin covering the tissue, and the hollow chamber being connected to a low pressure-producing element via a channel, and
a sensor or sensor system disposed on the channel, and/or a sensor or sensor system being integratable into a wall of the hollow chamber;
wherein the sensor system is configured as a plate-shaped element in which at least one containment is introduced, the containment tapering from the surface on the plate-shaped element in the direction of a surface oriented towards the channel, an oppositely-situated surface in which the containment is coated with electrodes and, in the containments, a membrane material is contained, the membrane surfaces of which, oriented in the direction of the channel, are in contact wit the liquid transported through the channel.

27. A method for removing liquid from endogenic tissue and determining concentrations of substances in this liquid, comprising:
placing a device on a skin surface, the device having at least one contact opening configured on at least one hollow chamber in a contact surface,
setting a low pressure in the hollow chamber and, forming a liquid reservoir underneath the skin surface,
collecting the liquid in the liquid reservoir, subsequently flowing the liquid from the liquid reservoir out of the tissue and guiding the liquid with suction forces occasioned by low pressure to a sensor or a sensor system, which is disposed on the channel or is integrated in the wall of the hollow chamber, and measuring a complex electrical resistance between a penetration element and an electrode in contact with the surface of the skin.

28. The method according to claim 27, further comprising penetrating at least an uppermost skin layer lying above the liquid reservoir after formation of the liquid reservoir with the help of a penetration element disposed in the hollow chamber or guidable through the contact opening of the hollow chamber in the direction of the skin.

* * * * *